(12) United States Patent
Thraves et al.

(10) Patent No.: US 7,303,911 B2
(45) Date of Patent: Dec. 4, 2007

(54) PROSTATE CELL LINES

(75) Inventors: Peter Thraves, London (GB); Andrew Sutton, London (GB)

(73) Assignee: Onyvax Limited (GB)

( * ) Notice: Subject to any disclaimer, the term of this patent is extended or adjusted under 35 U.S.C. 154(b) by 349 days.

(21) Appl. No.: 10/240,523

(22) PCT Filed: Mar. 30, 2001

(86) PCT No.: PCT/GB01/01437

§ 371 (c)(1),
(2), (4) Date: Oct. 23, 2002

(87) PCT Pub. No.: WO01/75073

PCT Pub. Date: Oct. 11, 2001

(65) Prior Publication Data

US 2003/0185808 A1    Oct. 2, 2003

(30) Foreign Application Priority Data

Apr. 1, 2000  (GB) ................................. 0008032.5
Oct. 3, 2000  (GB) ................................. 0024237.0

(51) Int. Cl.
  *C12N 15/85* (2006.01)
  *C12N 15/86* (2006.01)
(52) U.S. Cl. .................................... 435/325
(58) Field of Classification Search ................ 435/325; 424/277.1
See application file for complete search history.

(56) References Cited

FOREIGN PATENT DOCUMENTS

| WO | WO97/18296 | 5/1997 |
|----|------------|--------|
| WO | WO97/24132 | 7/1997 |
| WO | WO97/28255 | 8/1997 |
| WO | WO98/16238 | 4/1998 |
| WO | WO99/19462 | 4/1999 |
| WO | WO00/04918 | 2/2000 |
| WO | WO00/33869 | 6/2000 |
| WO | WO00/71155 A2 | 11/2000 |

OTHER PUBLICATIONS

Gura (Science, v278, 1997, pp. 1041-1042).*
Weiner L.M., Seminars Oncology, vol. 26, No. 4, Suppl 12, pp. 41-50, 1999.*
Bellone et al. . (Immunology Today, v20 (10), 1999, pp. 457-461.*
Freshney (Culture of Animal Cells, A Manual of Basic Technique, Alan R. Liss, Inc., 1983, New York, p. 4.*
Dermer (Bio/Technology, 1994, 12:320).*
Ablin, J. Cancer Res. Clin. Oncol. 123: 583-594 (1997).
Berthon et al., Intl. Journal of Oncology 6:333-343 (1995).
Brenner et al., Journal of Urology, pp. 1575-1579 (1995) (abstract only).
Gorelik et al., Journal of Supramolecular Structure 12: 385-402 (1979) (abstract only).
Marble, Cancer Weekly Plus, p. 4(2) (1997).
Moran, American Medical News 42, 39, 23 (1999).
Tjoa et al., The Prostate 27: 63-69 (1995).
Zhau et al., Proc. Natl. Acad. Sci. USA 93: 15152-15157 (1996).
Freshney, "Culture of Animal Cells", Chapter 23, p. 314 (1987).
Olumi et al., Cancer Research 58: 4525-4530 (1998).

* cited by examiner

*Primary Examiner*—Christopher Yaen
(74) *Attorney, Agent, or Firm*—Proskauer Rose LLP (57) ABSTRACT

An increasingly aged population and better diagnosis has lead to an apparent increase in the prevalence of prostate cancer in men. There is an acute need to better understand the progression of this disease from its locally confined site of initiation to the end stage widely metastatic disease with attendant morbidity and mortality, It has historically been difficult to raise and maintain immortalized prostate cell lines in culture. We have derived a cell line selected from the group consisting of clones ONYCAP 1 and ONYCAP23. The cell lines are characterized as being prostate epithelial in origin.

16 Claims, 10 Drawing Sheets

A = Isotype control plot
B = Specific antibody staining

Figure 2b

A = Isotype control plot
B = Specific antibody staining

Figure 3Ai: Onycap1-

A = Isotype control plot
B = Specific antibody staining

Figure 3Aii

A = Isotype control plot
B = Specific antibody staining

Figure 3Aiii

A = Isotype control plot
B = Specific antibody staining

Figure 3Bi:- Onycap 23

A = Isotype control plot
B = Specific antibody staining

Figure 3Bii

A = Isotype control plot
B = Specific antibody staining

Figure 3Biii

A = Isotype control plot
B = Specific antibody staining

Figure 4:

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:
      Illustrative endoplasmic reticulum retention signal motif

<400> SEQUENCE: 1

Lys Asp Glu Leu
1
```

PROSTATE CELL LINES

This application is a 371 of PCT/GB01/01437 filed on Mar. 30, 2001, which is hereby incorporated by reference.

SUMMARY

An increasingly aged population and better diagnosis has lead to an apparent increase in the prevalence of prostate cancer in men. There is an acute need to better understand the progression of this disease from its locally confined site of initiation to the end stage widely metastatic disease with attendant morbidity and mortality. It has historically been difficult to raise and maintain immortalised prostate cell lines in culture. For some 15-20 years the field of in vitro experimentation in prostate cancer has relied upon three cell lines derived from metatstatic sites. More recently several new cell lines have been derived from primary tissue by means of immortalisation with viral oncogene constructs. We have derived a series of immortal cell line clones. The cell lines are characterised as being prostate epithelial in origin and have excellent growth characteristics in combination with unusual expression of markers that make these cell lines valuable for antigen discovery and use as potential vaccines in the treatment of prostate cancer as well as for the purposes of drug screening, genetic analysis of the basis of prostate cancer and other relevant studies.

FIELD OF THE INVENTION

Carcinoma of the prostate (PCA) is the second-most frequent cause of cancer related death in men in the United States (Boring, 1993). The increased incidence of prostate cancer during the last decade has established prostate cancer as the most prevalent of all cancers (Carter and Coffey, 1990). Although prostate cancer is the most common cancer found in United States men, (approximately 200,000 newly diagnosed cases/year), the molecular changes underlying its genesis and progression remain poorly understood (Boring et al., 1993).

An unusual challenge presented by prostate cancer is that most prostate tumors do not represent life threatening conditions. Evidence from autopsies indicate that 11 million American men have prostate cancer (Dbom, 1983). These figures are consistent with prostate carcinoma having a protracted natural history in which relatively few tumors progress to clinical significance during the lifetime of the patient. If the cancer is well-differentiated, organ-confined and focal when detected, treatment does not extend the life expectancy of older patients.

Unfortunately, the relatively few prostate carcinomas that are progressive in nature are likely to have already metastasized by the time of clinical detection. Survival rates for individuals with metastatic prostate cancer are quite low. Between these two extremes are patients with prostate tumors that will metastasize but have not yet done so. For these patients, surgical removal of their prostates is curative and extends their life expectancy.

Historically there have been few immortal prostate lines which may be cultured in vivo for use in drug screening, antigen discovery or other experimental techniques seeking new therapeutic entities for this disease. Three cell lines have been in widespread experimental use for some 15-20 years namely; DU145, (Mickey, et al., Cancer Res. 37: 4049-4058, 1977; K. R. Stone, et al., Int. J. Cancer 21: 274-281, 1978); PC-3, (M. E. Kaighn et al Invest. Urol. 17: 16-23, 1979; Cancer Res. 40: 524-534, 1980) and LnCap (Horoszewicz J. S. et al, Models for Prostate Cancer, 1980, Alan R, Liss Inc, 150 Fifth Avenue, New York N.Y. N.Y. 10011).

More recently a growing number of groups have developed new cell lines utlising virally derived oncogenes to achieve immortal status in culture. These cell lines include ; TSU-Pr1, (Iizumi T et al. J Urol June 1987 ; 137(6):1304-6, Establishment of a new prostatic carcinoma cell line TSU-Pr1); LuCap23 (Ellis W J. et al, *Clin Cancer Res* June 1996;2(6):1039-48, Characterization of a novel androgen-sensitive, prostate-specific antigen-producing prostatic carcinoma xenograft: LuCaP 23); P69SV40-T P69-M2182, (Plymate S R. et al *J Clin Endocrinol Metab* October 1996; 81(10):3709-16, The effect on the insulin-like growth factor system in human prostate epithelial cells of immortalization and transformation by simian virus-40 T antigen); MDA PCa 2a and MDA PCa 2b (Navone N M. et al., *Clin Cancer Res* December 1997; 3(12 Pt 1):2493-500 Establishment of two human prostate cancer cell lines derived from a single bone metastasis); 1519-CPTX, 1535-CPTX, 1532-CPTX and 1542-CP$_3$TX (Bright R K. et al., Cancer Res Mar. 1, 1997;57(5):995-1002 Generation and genetic characterization of immortal human prostate epithelial cell lines derived from primary cancer specimens) and the ARCAP cell line (Zhau H. Y. et al Androgen-repressed phenotype in human prostate cancer *Proc Natl Acad Sci USA* Dec. 24, 1996;93(26):15152-7)

Prostate cancer in situ and also cell lines from primary and metastatic sites in common with many tumour types have been shown to down regulate their MHC-I expression by a variety of mechanisms (Blades R A et al Urology November 1995;46(5):681-6; discussion 686-7 Loss of HLA class I expression in prostate cancer: implications for immunotherapy). This has implications for immunotherapeutic strategies in vivo and also antigen discovery in vitro both of which benefit significantly from MHC-1 expression. In vivo, lack of MHC-1 expression will disable the direct presentation by tumour cells of T cell epitopes to the T cell receptor on both CD4 and CD8 cells and thereby effectively become invisible to T cell mediated killing. In vitro immortalised cells lacking MHC-1 expression are significantly less effective in a number of experimental uses including T cell mediated lysis assays and peptide elution studies. Therapeutic uses of cell lines in the form of whole cell vaccines also benefit from MHC-1 expression, particularly in allogeneic vaccination strategies. In experimental models of vaccination against tumour challenge "allo" MHC-1 expression in the vaccinating cell line produces the most marked protective effect particularly when the allo MHC-1 resides on the tumour cell carrying relevant tumour associated or tumour specific antigens (Xu W et al Cancer Immunol Immunother January 1998;45(5):217-24).

SPECIFIC FIELD OF THE INVENTION

Prostate cancer in most cases remains localised within the prostate itself and does not escape the local confines of the prostate. Thus unless patients are monitored clinically by way of blood PSA level, digital rectal examination, ultrasound or needle biopsy the lesion is not diagnosed. When the tumour does escape from the prostate gland the spread and the favoured metastatic sites are very reproducible. The main sites of deposition are the local lymph nodes and more extensively the bone, in fact very often the first diagnosis of prostate disease is bone pain or non specific fractures of the bone resulting from bone metastatic deposits. The reasons for the preponderance of lymph and bone metastasis may be the local proximity of the lymph nodes and the growth factor rich environment of the bone. There have been relatively few reports of cell lines generated from other metastatic sites, the most notable being the derivation of DU145 from a brain metastasis and the ARCAP cell line derived also from ascitic fluid of a patient with widely disseminated prostate cancer.

The first embodiment of this invention is two cell clones ONYCAP1 and ONYCAP23. The cell lines have been extensively characterised as being prostate epithelial in origin by virtue of cytokeratin staining. The cell lines are further shown to posses significant levels of surface MHC-1 expression in addition to several other immune functional proteins not normally attributed to tumour cell lines, namely MHC-2, ICAM, and CD40 ligand. The two clones show differing morphology and also a differing pattern of gene expression with Onycap23 showing a distinct osteomimetic phenotype compared to Oncap1.

In our application number GB 0008032.5 (Jan. 4, 2000) we believed that these cells derived from the ascitic fluid but we now know they are derived from PNT-2 cells (see the Examples).

A second embodiment of this invention is the use of any one of the cell lines in the formulation of a vaccine for the treatment of prostate cancer with or without a vaccine adjuvant which may include Il-2, IL-12, interferon gamma, BCG, tetanus toxoid or Mycobacterium Vaccae. The vaccine may be used as an adjuvant therapy in combination with other treatment modalities such as radiotherapy, or surgery or chemotherapy where the vaccine is used to treat or resolve minimal residual disease.

A further aspect of the invention is the use of a combination of the cell lines in the formulation of a vaccine for the treatment of prostate cancer with or without a vaccine adjuvant which may include Il-2, IL-12, interferon gamma, BCG, tetanus toxoid or Mycobacterium Vaccae. The vaccine may be used as an adjuvant therapy in combination with other treatment modalities such as radiotherapy, surgery or chemotherapy where the vaccine is used to treat or resolve minimal residual disease A further aspect of the invention is the use of a combination of any of the cells with other prostate cell lines available from ATCC, ECACC or other laboratories and cell banks in the formulation of a vaccine for the treatment of prostate cancer with or without a vaccine adjuvant which may include IL-2, IL-12, interferon gamma, BCG, tetanus toxoid, Mycobacterium Vaccae or another suitable adjuvant or immunomodulator known in the art. The vaccine may be used as an adjuvant therapy in combination with other treatment modalities such as radiotherapy, surgery or chemotherapy where the vaccine is used to treat or resolve minimal residual disease or for the treatment of the disease at any stage with or without co-treatment of various types.

An unexpected finding arising from the analysis of these cell lines is the finding that they possess significant surface levels of MHC-1 which offers the potential to use the cell lines in peptide elution studies to isolate and identify MHC-1 restricted peptides from these cell lines. These cell lines are also unique both in the spontaneous nature of their immortalisation and the highly aggressive manner in which they have developed in vivo. They therefore represent an excellent source of potential antigens relevant for metastatic prostate disease. A further embodiment of this invention is therefore the use of these cell lines to identify MHC-1 restricted peptides and tumour antigens, peptides and proteins arising from these cell lines and vaccines prepared utilising antigens, peptides or DNA vaccines derived from these cell lines.

A further embodiment of this invention are expression libraries derived from the cell lines which can be used in screening experiments to discover tumour associated or specific antigens for use as vaccine or immunotherapies and diagnostics. Expression cloning is now technically simple utilising commercially available kits such as the epitope tagged bacterial expression kits from Invitrogen™ and Roche™ or mammalian expression kits from Statagene™. Once the RNA has been reverse transcribed to cDNA and inserted into a relevant expression system the various clones can be probed with anti-serum from vaccinated or non vaccinated patients using a SEREX type approach. Alternatively mammalian cell expression clones can be used as targets for use with cytotoxic T-cells (CTL) from vaccinated or unvaccinated animals or patients to identify potential T cell antigens.

In a further embodiment the cell lines may be used in specific proliferation experiments utilising whole blood to determine the precursor frequency of T cells that recognise antigens derived from the cell lines in both vaccinated and non-vaccinated patients. We have surprisingly found that lysates of these cell lines are good at stimulating T cell proliferation in a high percentage of non-vaccinated patients indicating that there may be many shared antigens between these novel cell lines and early stage tumours in situ. Lysates of the cells may also be used to pulse antigen presenting cells or other cells expressing MHC-1 to enable these cells to be used as potential targets in CTL assays.

Further embodiments of this invention relate to use of the cell lines grown in nude mice for drug screening, use of the cell lines in genomic screens for drug target identification and identification of antigens which may be used in diagnostic assays to screen for early phase detection of prostate cancer.

DESCRIPTION OF FIGURES

FIG. 1: Morphology of Onycap 1 (×200 FIG. 1A) and Onycap 23 (×200 FIG. 1B)

EXAMPLES

Isolation of the Cell Lines

A sample of ascitic fluid (3L) was drawn from a patient with known metastatic prostate disease. The ascitic fluid was centrifuged at 1000×g for 15 minutes and then resuspended in KSFM media supplemented with 25 g/ml bovine pituitary extract, 5 ng/ml of epidermal growth factor, 2 mM L-glutamine, 10 mM HEPES buffer and 5% foetal calf serum (FCS) (hereinafter called "modified KSFM"). Initial outgrowth was monitored and the decanted media was centrifuged to retain any of the non-adherent cells. Over three to four weeks the spheroids attached and uniform cell populations were observed to grow out onto the T75 flasks. It is believed that at some stage during outgrowth contamination occurred with cells PNT-2 [ECACC Reference Number 95012613] which are prostate epithelial cells immortalised with SV40 Large T antigen.

Cloning Out the Cell Lines

A T175 flask of the ascitic outgrowth was trypsinised and plated out onto 96 well tissue culture plates at varying dilutions calculated to give 1, 10 and 100 cells per well. After a period of 14-21 days growth clones were picked from the 1 cell/well plate where there were less than 20 colonies per plate visible. Identified clones were trypsinised and plated into T25 flasks for expansion, after some 14-21 days growth the clones were further expanded to T75 and thereafter T175 flasks. The expanded clones were trypsinised and reformulated in freezing mixture comprising KSFM containing 10% v/v FCS and 20% v/v DMSO and then stored in $1 \times 10^6$ cell aliquots in liquid nitrogen.

Characterisation of the Clones' Morphology

Figure 1A:
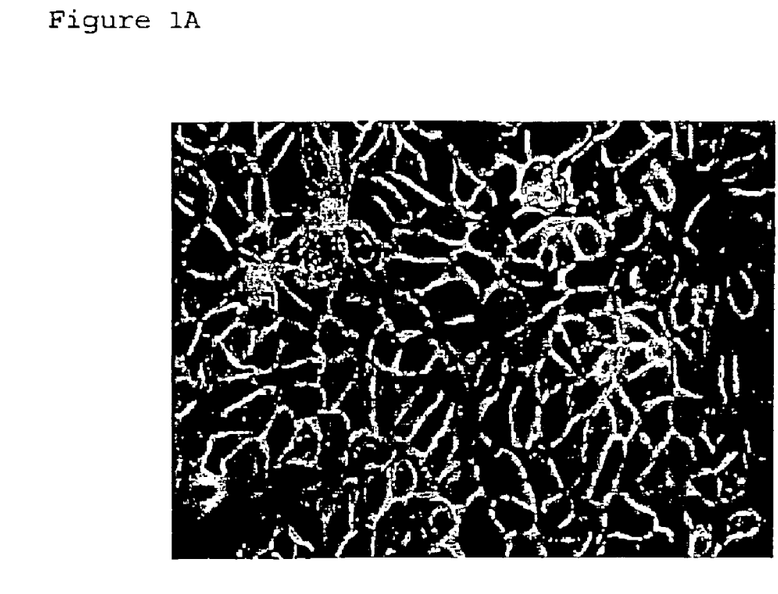
Figure 1B:
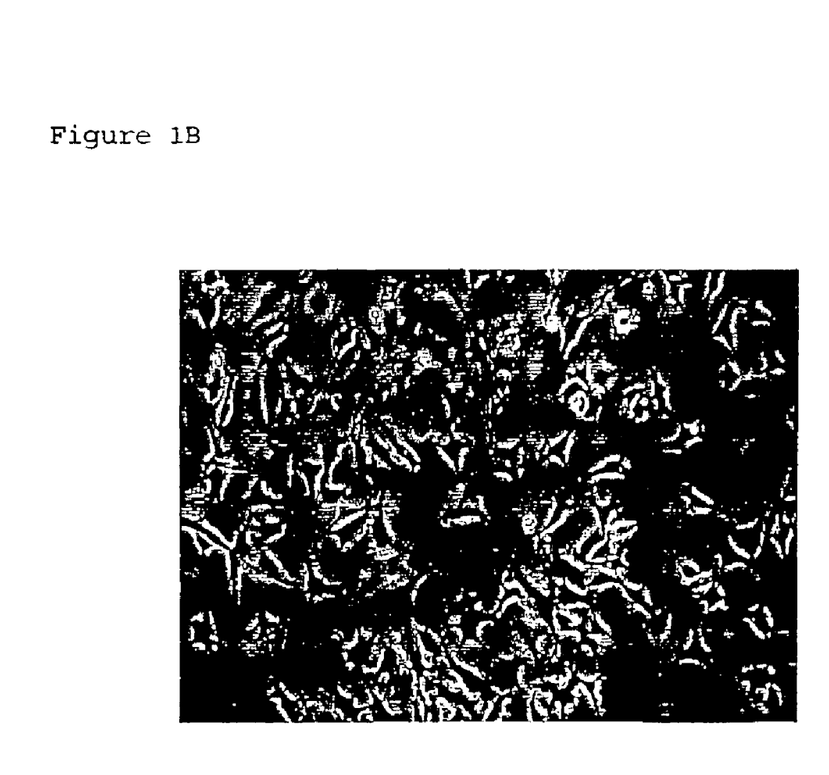

The various clones were characterised on the basis of morphology initially, and example photographs are depicted in FIG. 1. A small epithelial morphology is shown in FIG. 1A and is representative of clone Onycap1. A second unique morphology shown by clone Oncap23 is shown in FIG. 1B whereby the cells show dendrite-like processes emanating from a central cellular body similar to the so-called neuroendocrine phenotype (Chung T D K and Spiotto M T 2000 The Prostate 42 p186-195) which can be elicited by growth in IL6 containing medium.

Characterisation of the Clones as Being of Prostate Epithelial Origin

Figure 2A:
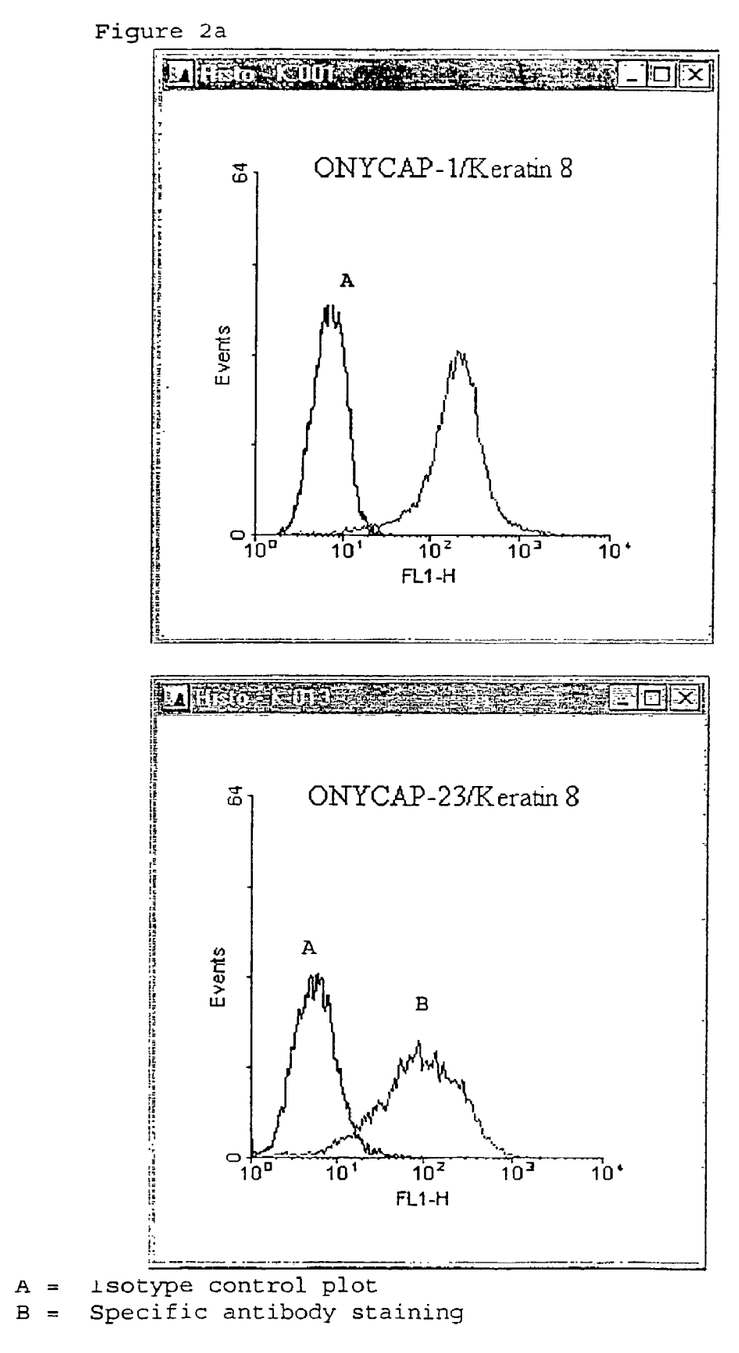
FIG. 2: FACS Analysis of Cytokeratin Expression by Onycap1 and Oncap23
Figure 2B:
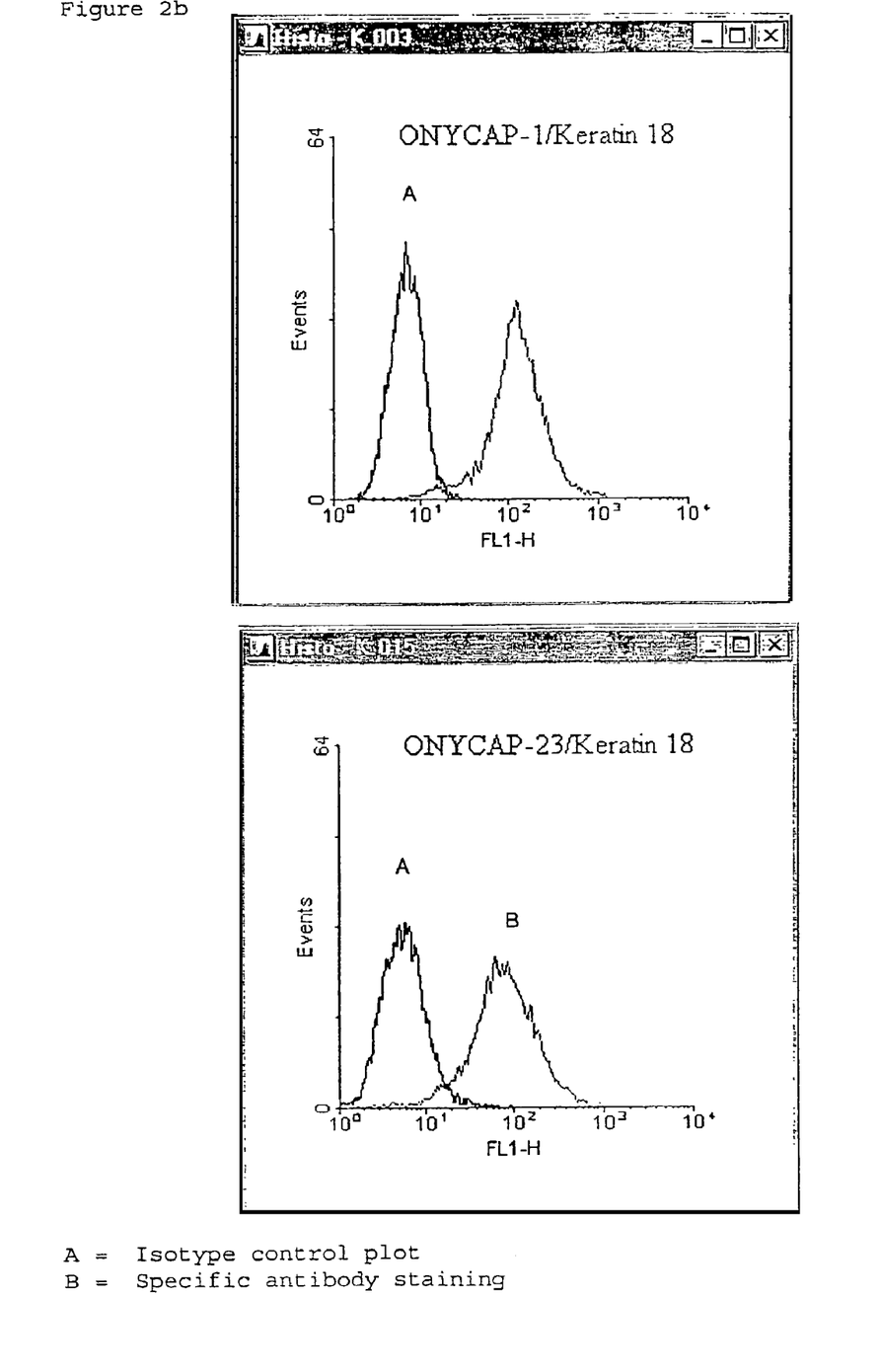

Onycap1 and Oncap23 clones have been analysed by flow cytometry using anti-cytokeratin 8, anti-cytokeratin 18 and desmin antibodies. Cytokeratin 8 and 18 are characteristic and considered true markers of prostatic epithelia. FIG. 2 shows examples of the flow cytometry analysis of the clones with CY8, CY18 and desmin antibodies compared with isotype control. In all cases the clones stained for these characteristic prostate epithelial markers proving their prostatic origin consistent with the medical condition of the patient.

Surface Marker Analysis of the Clones

Figure 3:
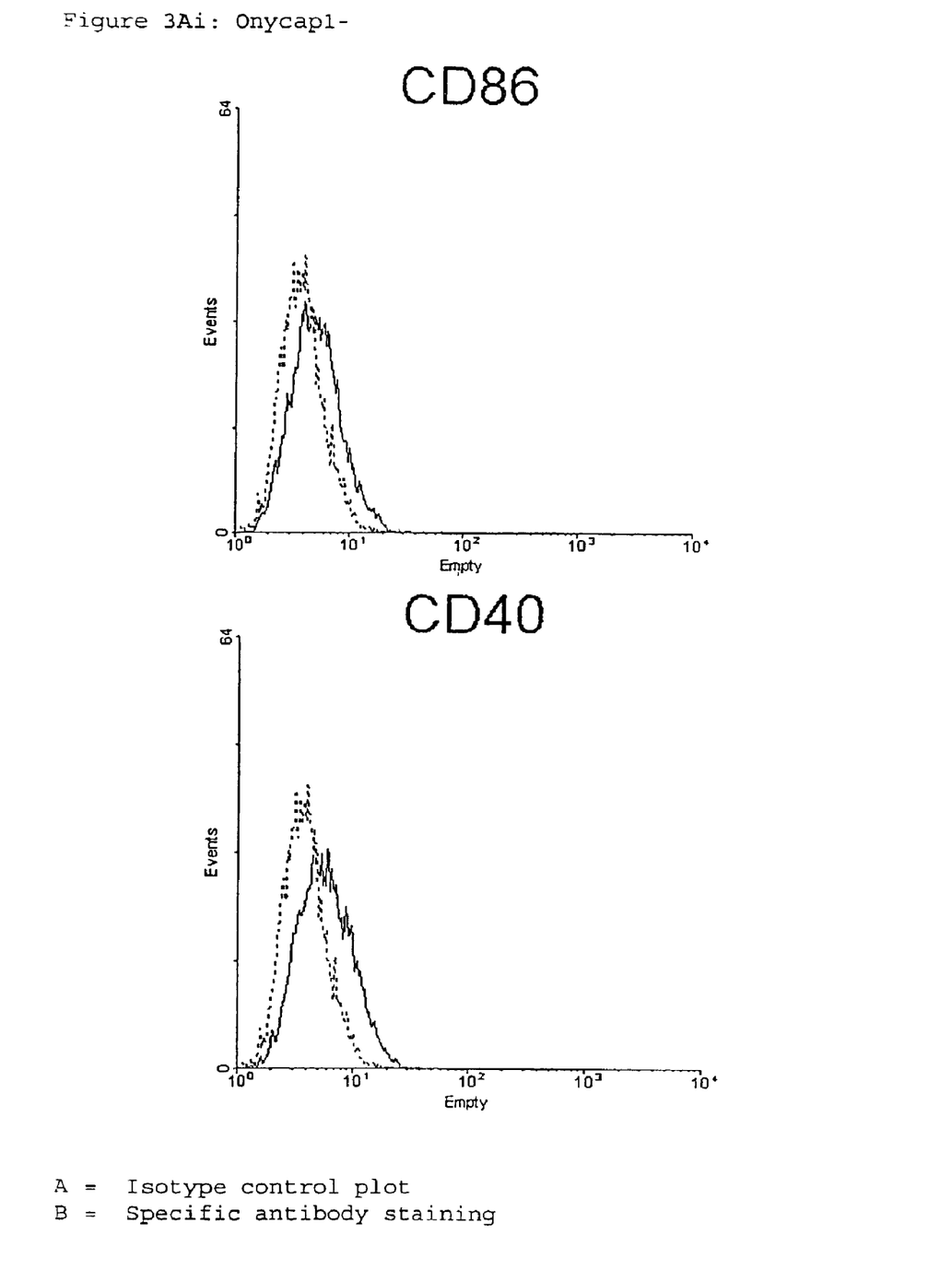
FIG. 3: FACS Analysis of Known Immunological Surface Markers Onycap1 (FIG. 3A) and Oncap23 (FIG. 23)

Selected clones were chosen for surface marker analysis using commercially available antibodies. Analysis was performed to detect the following proteins: MHC-I, MHC-II, CD40, CD154, CD69, CD80 and CD86. FIG. 3 shows representative flow cytometry data for Onycap1 and Oncap23. Unusually for prostate metastatic cell lines these clones show significant levels of MHC-I along with several other important markers which are important in cell based tumour immunotherapeutics, such as CD86 and CD40.

The presence of significant MHC-I levels is important since its cell surface presence will be important in eliciting an allogenic response when these cells are used as an whole cell allogeneic vaccine. There is also the possibility that with surface MHC-I expression these cells may also present directly to T cells, small peptide antigens restricted by the MPA clones MHC-I. In addition once the T cell receptor is engaged the presence of co-stimulatory molecules on the MPA clones may also elicit a significant proliferative response since both T receptor and co-stimulatory signals are present on the MPA cells.

cDNA Production and PCR Analysis of the Clones

Characterisation of the expression profile of Onycap1 and Oncap23 clones was performed by rtPCR analysis with a small number of PCR primers. The expression profile of several well known prostate proteins and antigens in addition to known markers of invasion and metastasis was undertaken to make a preliminary evaluation of these clones to compare them to other known prostate cells. Clones were grown in T75 flasks in KSFM media supplemented with 25 g/ml bovine pituitary extract, 5 ng/ml of epidermal growth factor, 2 mM L-glutamine, 10 mM HEPES buffer and 5% foetal calf serum (FCS).

Cell Culture

Cell lines ONYCAP-1 and ONYCAP-23, clones were grown in T75 flasks in modified KSFM. Cells were harvested by trypsinisation from the surface of the plastic and washed in Hanks balanced salt solution before RNA extraction.

RNA Extraction

A double extraction was performed using TRI REAGENT (Sigma #T9424). The reagent was added directly to the washed cell pellets and samples were allowed to stand for 5 minutes before the addition of chloroform. Samples were vortexed and allowed to stand for a further 10 minutes at room temperature then centrifuged at 12,000×g for 15 minutes.

The upper aqueous phase was transferred to a fresh tube, another aliquot of TRI REAGENT added and the above steps were repeated for the second stage extraction. The aqueous phase was again transferred to a fresh tube and the RNA precipitated with isopropanol. RNA pellets were washed with 75% ethanol, dried and re-suspended in TE buffer.

DNase Treatment

An aliquot of each RNA sample was treated with Deoxyribonuclease I (Life Technologies #18068-015) to ensure there was no contamination with genomic DNA. Reactions were incubated for 15 minutes at room temperature then the DNase was inactivated by the addition of 25 mM EDTA and heating to 65° C. for 10 minutes.

Reverse Transcription

Reverse transcription was performed using the 1st strand cDNA synthesis kit for RT-PCR (AMV) from Boehringer Mannheim (#1 483 188). Reactions were incubated at 25° C. for 10 minutes then at 42° C. for 1 hour. The AMV enzyme was denatured by heating to 99° C. for 5 minutes then the reaction was cooled to 4° C.

Results

PCR primers listed were selected from the literature to cover known prostate proteins, antigens and markers of invasion and metastasis. The cDNA extracted from the clones was probed with the primers and products of the reaction run out on high resolution agarose gels to check for products of the expected sizes. The results are tabulated in Table 1 for clones Onycap1 and Oncap23.

cDNA Production and DNA Array Analysis of the Clones

Methodology

Cell Culture

Cell line Onycap1 and Oncap23 were seeded at $1 \times 10^6$ cells into T175 culture flasks. Cultures were maintained for 4-5 days in modified KSFM. Cells were harvested by trypsinisation from the surface of the plastic and washed in Hanks balanced salt solution before RNA extraction.

RNA Extraction

A double extraction was performed using TRI REAGENT (Sigma #T9424). The reagent was added directly to the washed cell pellets and samples were allowed to stand for 5 minutes before the addition of chloroform. Samples were vortexed and allowed to stand for a further 10 minutes at room temperature then centrifuged at 12,000×g for 15 minutes.

The upper aqueous phase was transferred to a fresh tube, another aliquot of TRI REAGENT added and the above steps were repeated for the second stage extraction. The aqueous phase was again transferred to a fresh tube and the RNA precipitated with isopropanol. RNA pellets were washed with 75% ethanol, dried and re-suspended in TE buffer.

DNase Treatment

An aliquot of each RNA sample was treated with Deoxyribonuclease I (Life Technologies #18068-015) to ensure there was no contamination with genomic DNA. Reactions were incubated for 15 minutes at room temperature then the DNase inactivated by the addition of 25 mM EDTA and heating to 65° C. for 10 minutes.

DNA Array Probing

Labelled cDNA was used to probe a Clontech Atlas™ array (human cancer array II) following the manufacturers protocol for hybridisation and washing. Images were recorded utilising a phosphor imager and recorded files analysed with the Clontech Atlas Image™ software.

Results

Expressed genes are tabulated in Table 2 and show the clones Onycap1 and Oncap23 to share many common expressed genes but also that they possess unique expressed products as predicted by their very different morphology Human T Cell Proliferative Response to Lysates of Onycap1 and Oncap23

Methodology

Preparation of MPA Clone Lysates for T Cell Proliferation Studies.

Clones were grown in T75 flasks in modified KSFM. Once the cells have reached confluency they were harvested by trypsinisation and washed in Hanks balanced salt solution and then pelleted by centrifugation.

The pelleted cell mass was taken through four freeze thaw cycles in a minimal volume of Hanks balanced salt solution at a cell concentration of $2 \times 10^6$ cells/ml. The resulting cell supernatent was aliquoted into 25 ul aliquots and stored at −70° C. until required.

We performed a proliferation assay on T-cells from early stage prostate cancer patients following stimulation with lysates of the prostate cell lines, to determine if at an early stage of the disease T-cell populations harbored a reactivity to antigens derived from the Onycap1 and Oncap23 cell clones. Whole blood was extracted at each visit to the clinic and used in a BrdU (bromodeoxyuridine) based proliferation assay as described below:

Patient BrdU Proliferation Method

| Reagents | Catalogue # | Supplier |
|---|---|---|
| RPMI medium | | Life Technologies, Paisley Scotland. |
| BrdU | | Sigma Chemical Co, Poole, Dorset. |
| PharMlyse | 35221E | Pharmingen, Oxford UK |
| Cytofix/Cytoperm | 2090KZ | " |
| Perm/Wash buffer (×10) | 2091KZ | " |
| FITC Anti-BrdU/Dnase | 340649 | Becton Dickinson |
| PerCP Anti-CD3 | 347344 | " |
| Pe Anti-CD4 | 30155X | Pharmingen |
| Pe Anti-CD8 | 30325X | " |
| FITC mu-IgG1 | 349041 | Becton Dickinson |
| PerCP IgG1 | 349044 | " |
| PE IgG1 | 340013 | " |

Method

1) Dilute 1 ml blood with 9 ml RPMI+2 mM L-glutamine+penicillin/streptomycin antibiotics+50 μM 2-mercaptoethanol. Do not add serum. Leave overnight at 37° C.
2) On following morning, aliquot 450 μl of diluted blood into wells of a 48-well plate and add 50 μl of stimulator lysate. The lysate is made by freeze-thawing tumour cells ($2 \times 10^6$ cell equivalents/ml)×3 in liquid nitrogen and then storing aliquots frozen until required.
3) Culture cells at 37° C. for 5 days
4) On the evening of day 5 add 50 μl BrdU @ 30 μg/ml
5) Aliquot 100 μl of each sample into a 96-well round-bottomed plate.
6) Spin plate and discard supernatant
7) Lyse red cells using 100 μl PharMlyse™ for 5 minutes at room temperature
8) Wash ×2 with 50 μl of Cytofix™
9) Spin and remove supernatant by flicking
10) Permeabilise with 100 μl Perm/Wash™ for 10 mins at RT
11) Add 30 μl of antibody mix comprising antibodies at correct dilution made up to volume with Perm/Wash™
12) Incubate for 30 mins in the dark at room temperature.
13) Wash ×1 and resuspend in 100 μl 2% paraformaldehyde
14) Add this to 400 μl FACSFlow™ in cluster tubes ready for analysis
15) Analyse on FACScan™, storing 3000 gated CD3 events.

| 6-well plate for stimulation | | | | | |
|---|---|---|---|---|---|
| Nil | Con | 15 | Ln | D | Pn |
| PBL 1 | | | | | |
| PBL 2 | | | | | |
| PBL 3 | | | | | |
| PBL 4 | | | | | |
| PBL 5 | | | | | |
| PBL 6 | | | | | |

| 96-well plate for antibody staining | | | | | | | | | | | |
|---|---|---|---|---|---|---|---|---|---|---|---|
| PBL 1 | | PBL 2 | | PBL 3 | | PBL 4 | | PBL 5 | | PBL 6 | |
| Nil | 15 D | Nil | 15 D | Nil | 15 D | Nil | 15 D | Nil | 15 D | Nil | 15 D |
| A | | A | | A | | A | | A | | A | |
| Nil | 15 E | Nil | 15 E | Nil | 15 E | Nil | 15 E | Nil | 15 E | Nil | 15 E |
| D | | D | | D | | D | | D | | D | |
| Nil | Ln D | Nil | Ln D | Nil | Ln D | Nil | Ln D | Nil | Ln D | Nil | Ln D |
| E | | E | | E | | E | | E | | E | |
| Con | Ln E | Con | Ln E | Con | Ln E | Con | Ln E | Con | Ln E | Con | Ln E |
| D | | D | | D | | D | | D | | D | |
| Con | Du D | Con | Du D | Con | Du D | Con | Du D | Con | Du D | Con | Du D |
| E | | E | | E | | E | | E | | E | |
| | Du E | | Du E | | Du E | | Du E | | Du E | | Du E |
| | Pn D | | Pn D | | Pn D | | Pn D | | Pu D | | Pn D |
| | Pn E | | Pn E | | Pn E | | Pn E | | Pn E | | Pn E |

Figure 4:
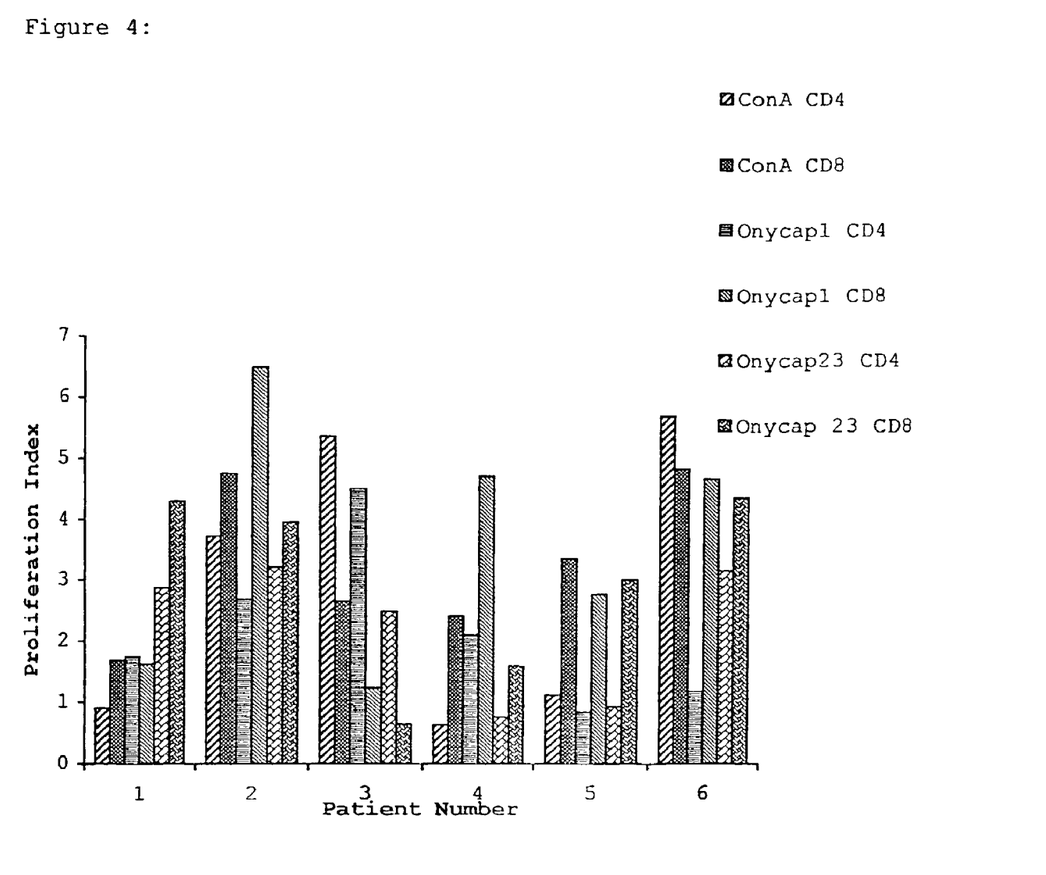
FIG. 4: Proliferation Response of Early Stage Prostate Cancer Patients to Lysates of Onycap1 and Oncap23

Legend:
A: FITC mu-IgG1 (5 μl) + PE IgG1 (5 μl) + PerCP IgG1 (5 μl) + 15 μl Perm/Wash ™
D: FITC Anti-BrdU/Dnase (5 μl) + Pe Anti-CD4 (5 μl) + PerCP anti-CD3 (5 μl) + 15 μl Perm/Wash ™
E: FITC Anti-BrdU/Dnase (5 μl) + Pe Anti-CD8 (5 μl) + PerCP Anti-CD3 (5 μl) + 15 μl Perm/Wash ™
15: NIH1542-CP3TX (an immortalised line derived from primary prostate cancers by Dr. Suzanne Topalian at the NIH)
Ln: LnCap (ATCC Number: CRL-1740)
D: Du145 (ATCC Number: HTB-81)
Pn: Pnt2 (ECACC Ref No: 95012613)
Con: ConA lectin (positive control)
Nil: No stimulation Results The results for a series of proliferation assays are shown in FIG. 4 where a proliferation index for either CD4 or CD8 positive T-cells are plotted against Onycap1 and Onycap 23 cell lysates, the proliferation index being derived by dividing the percentage of T-cells proliferating by the no-lysate control. A proliferation index above 1 indicates significant T cell proliferation in response to the cell lysate used to stimulate.

Results are shown for six early stage prostate patient sera 1, 2, 3, 4, 5 and 6 each of which was stimulated with Onycap1 or Oncap23 cell lysate. The results show that the Onycap cell lines posses antigens which differentially stimulate T cells from a variety of patients. Its is unlikely that a response is due to an mixed lymphocyte reaction since both cell lines posses the same haplotype and yet for each of the patients sera there are examples of one cell line stimulating a response where the other cell line does not.

TABLE 1

PCR Expression Analysis on Onycap1 and Oncap23

| Prostate Antigen | Onycap1 | Oncap23 |
|---|---|---|
| PSA | − | − |
| PAP | − | − |
| PSM | − | − |
| Androgen recptr. | − | − |
| EGF receptor | − | − |
| IGF-II | − | − |
| HGF receptor | + | + |
| uPA | + | + |
| PCTA-1 | + | + |
| PSCA | + | + |
| GRP receptor | − | + |
| uPA receptor | + | + |
| Hyaluronic acid receptor | − | − |
| MMP-9 | − | − |
| Vimentin | + | + |
| PAGE-1 | − | − |
| E-cadherin | − | − |
| TGFα | + | + |
| KAI1 | − | + |
| Heparanase | + | + |

TABLE 2

Gene Expression Analysis for Onycap1 and Oncap23 Spot Intensity

| Onycap1 | Oncap23 | Gene product |
|---|---|---|
| 2748 | 10332 | CD81 antigen; 26-kDa cell surface protein TAPA-1 |
| 2260 | 9368 | leukemia virus receptor 1 (GLVR1) |
| 0 | 7652 | lysosome-associated membrane glycoprotein 2 precursor (LAMP2); CD107B antigen |
| 0 | 5184 | lysosome membrane protein II (LIMP II); |
| 0 | 12796 | annexin V; lipo-cortin V; endo-nexin II; |
| 0 | 5688 | LGALS3, MAC2 (Galectin-3, MAC-2 antigen, |
| 0 | 6528 | lymphocyte function-associated antigen 3 precursor (LFA3); CD58 antigen |
| 0 | 28900 | neprilysin; neutral endopeptidase (NEP); enkephalinase (EPN); |
| 0 | 7264 | zinc finger protein |
| 248 | 2676 | 5'-TG-3' INTERACTING FACTOR (HOMEOBOXPROTEIN TGIF) |
| 0 | 5032 | HOMEOBOX PROTEIN SIX1 |
| 2504 | 4888 | SOX-9 PROTEIN |
| 1440 | 3128 | ZINC FINGER PROTEIN SLUG |

TABLE 2-continued

Gene Expression Analysis for Onycap1 and Oncap23 Spot Intensity

| Onycap1 | Oncap23 | Gene product |
|---|---|---|
| 0 | 6052 | ENX-1 PUTATIVE TRANSCRIPTIONAL REGULATOR |
| 804 | 7100 | LIM AND SH3 DOMAIN PROTEIN LASP-1 (MLN 50) |
| 388 | 4708 | MEL-18 RING-FINGER PROTEIN |
| 8716 | 17132 | NAT1 TRANSLATION REPRESSOR |
| 0 | 6312 | SAP18 (Sin3 associated polypeptide P18) |
| 0 | 6984 | preliminary PRT 640 AA RNA polymerase II elongation factor ELL2 |
| 1932 | 6228 | HLA-B-associated transcript 2; large proline-rich protein BAT2 |
| 11008 | 2132 | complement 3(C3) |
| 2076 | 8868 | LANP CEREBELLAR LEUCINE RICH ACIDIC NUCLEAR PROTEIN |
| 184 | 3164 | phospholipid transfer protein precursor (PTLP); lipid transfer protein II |
| 3016 | 12244 | dek protein |
| 0 | 5452 | CYSTEINE-RICH PROTEIN 2 (CRP2) (ESP1 PROTEIN) |
| 3748 | 8480 | RNA-binding protein EWS |
| 6200 | 15836 | RNA-binding protein fus/tls |
| 12996 | 35868 | nucleolar phosphoprotein B23; nucleophosmin (NPM); numatrin |
| 4532 | 12992 | platelet-derived growth factor (PDGF) receptor beta-like tumor suppressor (PRLTS) |
| 1680 | 5664 | retinoic acid receptor alpha |
| 1744 | 15192 | ras-related protein R-ras2; ras-like protein TC21; teratocarcinoma oncogene |
| 0 | 5676 | clathrin assembly protein lymphoid myeloid leukemia (CALM) |
| 27752 | 40916 | MT1H (Methallothionein-IH, Metallothinein-0, MT-0) + Metallothionein isoform 1L (MT-1L) |
| 9124 | 26864 | voltage-dependent anion-selective channel protein 1 (VDAC1); |
| 244 | 6964 | ras-related protein RAB-5C |
| 0 | 5584 | vesicle-membrane fusion protein SNAP23A |
| 3976 | 16024 | annexin IV (ANX4); lipocortin I; calpactin II; chromobindin 9; phospholipase A2 inhibitoiy protein |
| 13640 | 34420 | annexin I (ANX1) |
| 11428 | 27236 | annexin II (ANX2); lipocortin II; calpactin I heavy subunit; chromobindin 8; protein I; |
| 0 | 7944 | ER lumen protein retaining receptor 2; KDEL (SEQ ID NO: 1) receptor 2; ERD 22 |
| 0 | 5136 | protein SEC23 homolog isoform A (SEC23A) |
| 2896 | 11292 | coatomer beta' subunit; beta'-coat protein; beta'-COP; p102 |
| 0 | 5472 | coatomer delta subunit; delta-coat protein; delta-COP; archain (ARCN1) |
| 0 | 6448 | cation-dependent mannose-6-phosphate receptor precursor |
| 0 | 7516 | syntaxin 7 (STX7) |
| 3464 | 8192 | ras-related protein RAB-11B; YPT3 |
| 5740 | 9960 | ras-related protein RAB-7 |
| 3852 | 14512 | ras-related protein RAB-1A; YPTL-related protein |
| 640 | 4004 | calcium-binding protein p22; calcium-binding protein CHP |
| 0 | 9184 | clathrin coat assembly protein AP17; plasma membrane adaptor AP-2 17-kDa protein; |
| 8496 | 19328 | clathrin coat assembly protein AP50; plasma membrane adaptor AP-2 50-kDa protein; |
| 0 | 5908 | cytosolic acetoacetyl-coenzyme A thiolase |
| 312 | 7616 | beta-D-galactosidase precursor; lactase; acid beta-galactosidase; GLB 1 |
| 1212 | 7572 | 6-PHOSPHOFRUCTOKINASE, |
| 3492 | 7320 | pyruvate kinase M2 isozyme (PKM2) |
| 708 | 6620 | succinyl-CoA:3-ketoacid-coenzyme A transferase |
| 240 | 5856 | alcohol dehydrogenase 5 chi polypeptide |
| 0 | 5188 | NADH-cytochroine B5 reductase |
| 0 | 7152 | mitochondrial enoyl-CoA hydratase short subunit 1 |
| 0 | 5356 | 3-hydroxy-3-methylglutaryl-coenzyme A reductase (HMG-CoA reductase; HMGCR) |
| 0 | 5212 | lysosomal acid lipase/cholesteryl ester hydrolase precursor (LAL); |
| 0 | 8096 | phosphatidylethanolainine-binding protein (PBP); neuropolypeptide H3 |
| 0 | 6420 | annexin III (ANX3); lipocortin III; placental anticoagulant protein III) (PAP-III); |
| 432 | 5024 | farnesyl pyrophosphate synthetase |
| 448 | 5276 | H105E3 protein |
| 0 | 5084 | dihydrofolate reductase (DHFR) |
| 1976 | 8296 | thymidylate synthase (TYMS; TS) |
| 324 | 7856 | glutamate dehydrogenase 1 precursor (GDH; GLUD1) |
| 2580 | 5504 | very-long-chain-specific acyl-CoA dehydrogenase precursor (VLCAD) |
| 24144 | 34792 | femtin heavy chain (FTH1); FTHL6 |
| 44632 | 5996 | placental type 1 alkaline phosphatase precursor (PLAP-1) |
| 3732 | 8760 | homolog of yeast D2-isopentenylpyrophosphate isomerase (IPP isomerase) |
| 364 | 6132 | ornithine decarboxylase (ODC1) |
| 14304 | 24032 | protein disulfide isomerase |
| 0 | 5416 | cyclophilin 3 protein (CYP3); |
| 14884 | 31528 | 60S ribosomal protein L22 (RPL22); |
| 0 | 8068 | TIA-1 related protein; nucleolysin TIAR |
| 0 | 10204 | astrocytic phosphoprotein PEA-15 |
| 0 | 7020 | cyr61 protein precursor; GIG1 protein; insulin-like growth factor-binding protein 10 (IGFBP10) |
| 0 | 5668 | granulins precursor (GRN); acrogranin |
| 7288 | 16696 | natriuretic peptide precursor B |
| 932 | 3548 | SEMAPHORIN V |
| 660 | 8248 | signal transducing adaptor molecule (STAM) |
| 2096 | 4344 | beta-adaptin 1; plasma membrane adaptor HA2/AP2 adaptin beta subunit; |
| 128 | 5132 | RIBOSOMAL PROTEIN S6 KINASE (EC 2.7.1.-)(S6K) (P70-56K). |
| 2796 | 13364 | casein kinase I alpha isoform (CKI-alpha); CK1; CSNK1A |
| 11716 | 21668 | casein kinase I delta isoform (CKI-delta); CSNK1D |
| 812 | 6076 | casein kinase II beta subunit (CK II; CSNK2B; CK2N); phosvitin |
| 2204 | 7884 | MAP kinase-activated protein kinase 2 (MAPKAP kinase 2; MAPKAPK-2) |
| 0 | 5592 | protein phosphatase PP2A 65-kDa regulatory subunit alpha isoform; |
| 0 | 5292 | protein phosphatase PP2A 55-kDa regulatory subunit neuronal isoform; |
| 420 | 5744 | dual-specificity protein phosphatase 5; dual-specificity protein phosphatase HVH3 |
| 4328 | 10112 | dual-specificity protein phosphatase 7; dual-specificity protein phosphatase PYST2 |
| 1484 | 5124 | serine/threonine protein phosphatase 2B catalytic subunit alpha isoform; |
| 972 | 7260 | serine/threonine protein phosphatase 5 (PP5); protein phosphatase T (PPT) |
| 0 | 6016 | protein-tyrosine phosphatase 1B (PTP-1B) |
| 1584 | 6508 | protein-tyrosine phosphatase G1 (PTP-G1) |
| 6480 | 14912 | serine/threonine protein phosphatase PP1-alpha 1 catalytic subunit (PP-1A) |
| 952 | 6852 | guanine nucleotide-binding protein G(K) alpha 3 subunit (GNA3) |
| 4104 | 12748 | GUANINE NUCLEOTIDE-BINDING PROTEIN G(I), |
| 0 | 8304 | ras-related protein RAP-1B; GTP-binding protein SMG p21B |
| 0 | 6180 | calpactin I light chain |
| 8284 | 15236 | ras GTPase-activating-like protein IQGAP1; p19; KIAA0051 |
| 856 | 6416 | calmodulin |
| 1556 | 9264 | calmodulin |

TABLE 2-continued

Gene Expression Analysis for Onycap1 and Oncap23 Spot Intensity

| Onycap1 | Oncap23 | Gene product |
|---|---|---|
| 440 | 4164 | ANNEXIN XI (CALCYCLIN-ASSOCIATED ANNEXIN 50) (CAP-50) (56 KD AUTO-ANTIGEN). |
| 2756 | 8752 | calgizzarin; S100C protein; MLN70 |
| 3768 | 11592 | sorcin 22-kDa protein (SRI); CP-22 |
| 472 | 6296 | calcium signal-modulating cyclophilin ligand (CAML) |
| 5352 | 16056 | 14-3-3 protein beta/alpha; protein kinase C inhibitor protein-1 (KCIP-1); protein 1054 |
| 9088 | 20912 | 14-3-3 PROTEIN EPSILON (MITO-CHONDRIAL IMPORT STIMULATION FACTOR L SUBUNIT) |
| 4576 | 11468 | 14-3-3 PROTEIN ZETA/DELTA (PROTEIN KINASE C INHIBITOR PROTEIN-1) (KCIP-1) |
| 1688 | 8056 | phosphatidylinositol transfer protein alpha isoform (PI-TP-alpha; |
| 12604 | 26120 | guanine nucleotide-binding protein beta subunit-like protein 12; |
| 532 | 3800 | lysosomal protective protein precursor; cathepsin A; carboxypeptidase C; PPGB |
| 9808 | 23748 | calcium-dependent protease small (regulatory) subunit; calpain; |
| 1036 | 8220 | HUNTINGTIN INTERACTING PROTEIN (HIP2) |
| 0 | 5844 | lipoprotein-associated coagulation inhibitor |
| 504 | 4120 | protein-tyrosine phosphatase kappa precursor (R-PTP-kappa; PTPRK; PTPK) |
| 4740 | 14824 | PUTATIVE RECEPTOR PROTEIN (PM1) |
| 40 | 3116 | orphan receptor TR4 |
| 168 | 2980 | dynactin 150-kDa isoform; 150-kDa dynein-associated polypeptide (DAP-150; |
| 13744 | 33716 | COFILIN |
| 4044 | 12584 | alpha-actinin 1 cytoskeletal isoform; F-actin cross linking protein |
| 852 | 5288 | drebrinE |
| 1684 | 11556 | major prion protein precursor (PRP); PRP27-30; PRP33-35C; ASCR |
| 820 | 4628 | DXS6673E protein; X-linked mental retardation candidate gene |

The invention claimed is:

1. A cell line useful in immunotherapeutic treatment of prostate cancer, wherein the cell line is selected from the group consisting of clones ONYCAP-1 (ECACC 00032802) and ONYCAP-23 (ECACC 00032801).

2. A formulation for treatment of prostate cancer comprising any one of the cell lines of ONYCAP-1 (ECACC 00032802) and ONYCAP-23 (ECACC 00032801) and a pharmaceutically acceptable carrier.

3. A formulation for treatment of prostate cancer comprising a combination of the cell lines of ONYCAP-1 (ECACC 00032802) and ONYCAP-23 (ECACC 00032801) and a pharmaceutically acceptable carrier.

4. A formulation for treatment of prostate cancer comprising (A) a combination of (1) any of the cell lines selected from the group consisting of ONYCAP-1 (ECACC 00032802) and ONYCAP-23 (ECACC 00032801) with (2) at least one prostate cell line selected from the group consisting of DU145, PC-3, LnCap, TSU-Prl, LuCap23, P69SV40-T P69-M2182, MDAPCa 2a, MDA PCa 2b, 1519-CPTX, 1535-CPTX, 1532-CPTX and 1542-CP$_3$TX and ARCAP, and (B) a pharmaceutically acceptable carrier.

5. A formulation comprising cells from one or both cell lines of ONYCAP-1 (ECACC 00032802) and ONYCAP-23 (ECACC 00032801) and an adjuvant.

6. The formulation of claim 2, wherein the formulation further comprises an adjuvant selected from the group consisting of IL-2, IL-12, interferon gamma, BCG, tetanus toxoid or *Mycobacterium vaccae*.

7. The formulation of claim 3, wherein the formulation further comprises an adjuvant selected from the group consisting of IL-2, IL-12, interferon gamma, BCG, tetanus toxoid or *Mycobacterium vaccae*.

8. The formulation of claim 4, wherein the formulation further comprises an adjuvant selected from the group consisting of IL-2, IL-12, interferon gamma, BCG, tetanus toxoid or *Mycobacterium vaccae*.

9. A method for treating prostate cancer comprising administering to a subject a formulation comprising (A) a cell line selected from the group consisting of ONYCAP-1 (ECACC 00032802) and ONYOAP-23 (ECACC 00032801) and (B) a pharmaceutically acceptable carrier.

10. A method for treating prostate cancer comprising administering to a subject a formulation comprising (A) a combination of the cell lines selected from the group consisting of ONYCAP-1 (ECACC 00032802) and ONYCAP-23 (ECACC 00032801) and (B) a pharmaceutically acceptable carrier.

11. A method for treating prostate cancer comprising administering to a subject a formulation comprising (A) a combination of (1) at least one cell line selected from the group consisting of ONYCAP-1 (ECACC 00032802) and ONYCAP-23 (ECACC 00032801) with (2) at least one prostate cell line selected from the group consisting of DU145, PC-3, LnCap, TSU-Prl, LuCap23, P69SV40-T P69-M2182, MDAPCa 2a, MDA PCa 2b, 1519-CPTX, 1535-CPTX, 1532-CPTX and 1542-CP$_3$TX and ARCAP and (B) a pharmaceutically acceptable carrier.

12. A method for treating prostate cancer comprising administering to a subject a formulation, wherein the formulation comprises cells from one or both cell lines of ONYCAP-1 (ECACC 00032802) and ONYCAP-23 (ECACC 00032801) and an adjuvant.

13. The method of claim 9, wherein the formulation further comprises an adjuvant selected from the group consisting of IL-2, IL-12, interferon gamma, BCG, tetanus toxoid or *Mycobacterium vaccae*.

14. The method of claim 10, wherein the formulation further comprises an adjuvant selected from the group consisting of IL-2, IL-12, interferon gamma, BCG, tetanus toxoid or *Mycobacterium vaccae*.

15. The method of claim 11, wherein the formulation further comprises an adjuvant selected from the group consisting of IL-2, IL-12, interferon gamma, BCG, tetanus toxoid or *Mycobacterium vaccae*.

16. The method of claim 12, wherein the adjuvant is selected from the group consisting of IL-2, IL-12, interferon gamma, BCG, tetanus toxoid or *Mycobacterium vaccae*.

* * * * *